United States Patent [19]

Hsieh

[11] Patent Number: 5,450,461
[45] Date of Patent: Sep. 12, 1995

[54] SELF-CALIBRATING COMPUTED TOMOGRAPHY IMAGING SYSTEM

[75] Inventor: Jiang Hsieh, Waukesha, Wis.

[73] Assignee: General Electric Company, Milwaukee, Wis.

[21] Appl. No.: 175,905

[22] Filed: Dec. 30, 1993

[51] Int. Cl.6 .................... A61B 6/03; G01N 23/083
[52] U.S. Cl. ........................... 378/19; 378/901; 364/413.16
[58] Field of Search ............ 364/413.14, 413.15, 364/413.16, 413.17; 378/19, 901

[56] References Cited

U.S. PATENT DOCUMENTS

| | | | |
|---|---|---|---|
| 4,035,651 | 7/1977 | LeMay | 378/9 |
| 4,472,823 | 9/1984 | Waltham | 378/19 |
| 4,654,796 | 3/1987 | Takagi et al. | 364/414 |
| 5,301,108 | 4/1994 | Hsieh | 364/413.19 |

Primary Examiner—Paul M. Dzierzynski
Assistant Examiner—David Vernon Bruce
Attorney, Agent, or Firm—Quarles & Brady

[57] ABSTRACT

During acquisition of X-ray attenuation measurements of a patient being imaged, the measurements are processed to determine error factors for each detector in the system. In doing so, an average value is calculated for each detector from the X-ray attenuation measurements acquired during a scan of the patient. The set of average values should increase and decrease monotonically going toward and away from the value in the set for center detector. Deviation from such monotonic variation indicates a calibration error and is used to change a calibration factor in the signal processing circuit for the corresponding detector.

14 Claims, 4 Drawing Sheets

SELF-CALIBRATING COMPUTED TOMOGRAPHY IMAGING SYSTEM

BACKGROUND OF THE INVENTION

This invention relates to X-ray computed tomography (CT) imaging apparatus such as used in medical imaging; and more particularly to systems for calibrating the detector array in such apparatus.

In computed tomography, an X-ray source projects a fan-shaped beam which is collimated to lie within an X-Y plane of a cartesian coordinate system. The X-ray beam passes through an object being imaged, such as a medical patient, and impinges upon an array of radiation detectors. The intensity of the transmitted radiation is dependent upon the attenuation of the X-ray beam by the object and each detector produces a separate electrical signal that is a measurement of the beam attenuation. The attenuation measurements from all of the detectors are acquired separately to produce a transmission profile.

The source and detector array in a conventional CT system are rotated on a gantry within the imaging plane and around the object so that the angle at which the X-ray beam intersects the object constantly changes. A group of X-ray attenuation measurements from the detector array at a given angle is referred to as a "view" and a "scan" of the object represents a set of views made at different angular orientations during one revolution of the X-ray source and detector. The data for a given scan is stored in memory as a two-dimensional array with storage locations along one axis of the array representing the data from each radiation detector and the storage locations along the other axis containing data for the different views.

The scan data is processed to construct an image that corresponds to a two-dimensional slice taken through the object. The prevailing method for reconstructing the image is referred to in the art as the filtered backprojection technique. This process converts the attenuation measurements from a scan into integers called "CT numbers" or "Hounsfield units," which are used to control the brightness of a corresponding picture element on a cathode ray tube display.

In order for an image to be accurately constructed from the scan data, the signal processing circuitry for each detector in the array must be calibrated so that when a uniform level of radiation impinges each detector, the same magnitude signal will be produced from every processing circuit for the detectors.

Heretofore, the common technique for calibrating the detector array and processing circuits was referred to as the "air calibration technique." In performing this technique, the X-ray source was activated to produce a known intensity X-ray beam that was directed toward the detector array without any object being present therebetween. Ideally, this technique should produce the same level output signal from the processing circuit for each radiation detector. Any deviation of the signal of a given detector from a nominal level represented an error for that particular detector element. That erroneous signal level then was used in adjusting the gain of the signal processing circuit for the associated detector to produce the nominal output level during the air calibration.

If the detector arrays were relatively stable, the air calibration process needed to be only performed once a day. However, certain types of detector elements degraded with continuing exposure to X-rays. For these types of detector arrays, the air calibration technique had to be performed prior to imaging each patient. Even when air calibration needed to be performed only once a day, it consumed time that could otherwise be used for patient imaging. Therefore, it is desirable to reduce the frequency at which the detector array and its associated signal processing circuitry needs to be calibrated.

SUMMARY OF THE INVENTION

The general object of the present invention is to provide a method by which a computed tomography system can be recalibrated during the imaging of patients. Recalibration during patient imaging reduces the frequency at which the system has to be taken out of service to perform air calibration.

During an imaging scan of the patient, X-ray attenuation data samples are acquired from the detector array during each of a plurality of views. Normal preprocessing, such as air calibration, beam hardening correction and $-\log$, then is applied to these data to produce a set of projections. An average value is derived for each detector in the array from the plurality of X-ray attenuation data samples to produce a set of average values $\Omega(t)$ where t designates a given detector. Preferably the samples that are being averages were acquired from views covering one or more full 360° scans of the patient. Ideally the set of average values should decrease monotonically on either side of the average value for the center detector in the array. Any deviation from that monotonic decrease indicates an error in the calibration of the signal processing circuit for the corresponding detector.

To detect such deviation from the ideal, the set of average values $\Omega(t)$ is low-pass filtered to produce a set of filtered values $\Gamma(t)$. Since the deviations correspond to high frequencies in the detector signal, the low-pass filtering removes the deviation effects from the data. Each filtered value $\Gamma(t)$ is subtracted from its corresponding average value $\Omega(t)$ to produce a set of error values e(t). Each error value corresponds to a different detector and is employed to adjust the signal processing circuit for the corresponding detector.

In the preferred embodiment, any error values e(t) that are above a predefined threshold are considered not to be caused by detector gain and thus should not be employed in adjusting the corresponding signal processing circuit. Therefore, such error values are set to zero. Error values found to be significant are used to define a calibration factor GCAL(t) that sets the gain of an amplifier in the signal processing circuit for the associated detector. In the preferred embodiment, an error factor E(t) is derived by averaging the error values from several scans and then a new calibration factor GCAL(t) is calculated by multiplying the previous calibration factor by $e^E(t)$.

DESCRIPTION OF THE PREFERRED EMBODIMENT

Figure 1:
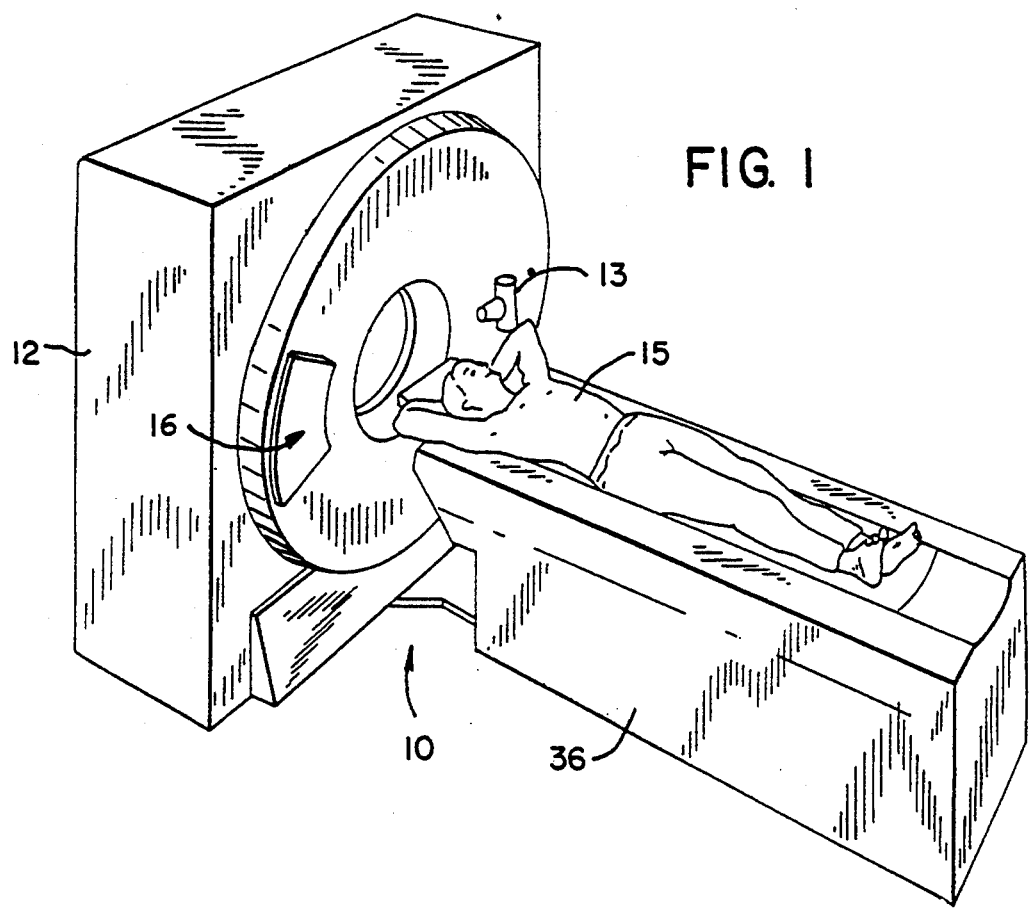
FIG. 1 is a pictorial view of a CT imaging system in which the present invention may be employed.
Figure 2:
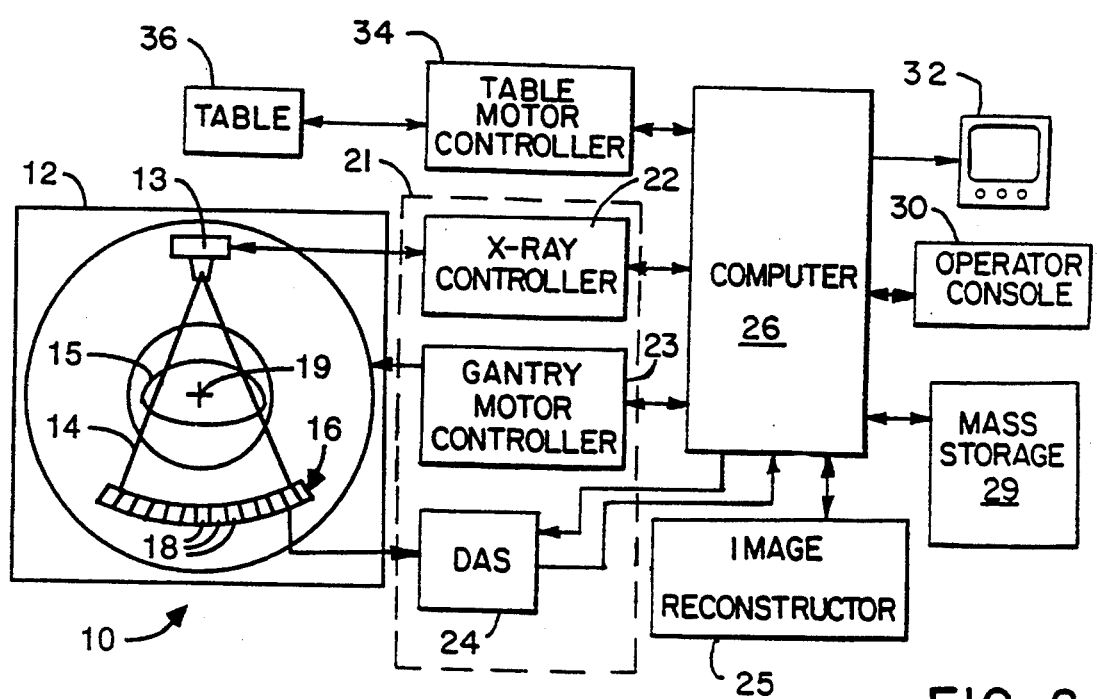
FIG. 2 is a block schematic diagram of the circuitry for the CT imaging system.

With initial reference to FIGS. 1 and 2, an X-ray computed tomography (CT) imaging system 10 includes a gantry 12 representative of a "third generation" CT scanner. Gantry 12 has an X-ray source 13 and projects a fan beam of X-rays 14 toward a detector array 16 on the opposite side of the gantry. The detector array 16 is formed by a member of individual detectors 18 which together sense the projected X-rays that pass through a medical patient 15. Each detector 18 produces an electrical signal that represents the intensity of an impinging X-ray beam and hence the attenuation of the beam as it passes through the patient. During a scan to acquire X-ray projection data, the gantry 12 and the components mounted thereon rotate about a center of rotation 19 located within the patient 15.

The rotation of the gantry 12 and the operation of the X-ray source 13 are governed by a control mechanism 20 of the CT system. The control mechanism 20 has a gantry associated control modules 21 which include an X-ray controller 22 that provides power and timing signals to the X-ray source 13 and a gantry motor controller 23 that controls the rotational speed and position of the gantry 12.

A data acquisition system (DAS) 24 in the control mechanism 20 samples analog projection data from detector elements 18 and converts that data into digital words which are stored for subsequent processing. The DAS circuitry has a separate signal processing channels for each detector element 18. In performing that conversion the DAS 24 also corrects for offset errors and other signal errors due to variation among the detectors and their individual signal channels. A separate calibration factor GCAL(t), where t indicates a given detector, is used to set the gain of amplifiers in each detector signal channel of the DAS 24 to correct for such channel dependent errors.

Thereafter, an image reconstructor 25, e.g. a standard array processor, receives the digitized samples of X-ray projection data and performs high speed image reconstruction according to methods known in the art. The reconstructed image is applied as an input to a computer 26 which stores the image data in a mass storage device 29.

The computer 26 also receives commands and scanning parameters from an operator via console 30 that has a keyboard; and an associated cathode ray tube display 32 allows the operator to observe the reconstructed image and other data from the computer. The operator supplied commands and parameters are used by the computer 26 to provide control signals and information to the DAS 24. The X-ray controller 22 and the gantry motor controller 23. Computer 26 also operates a motor controller 34 which controls a motorized table 36 to position the patient 15 in the gantry 12.

Figure 3:
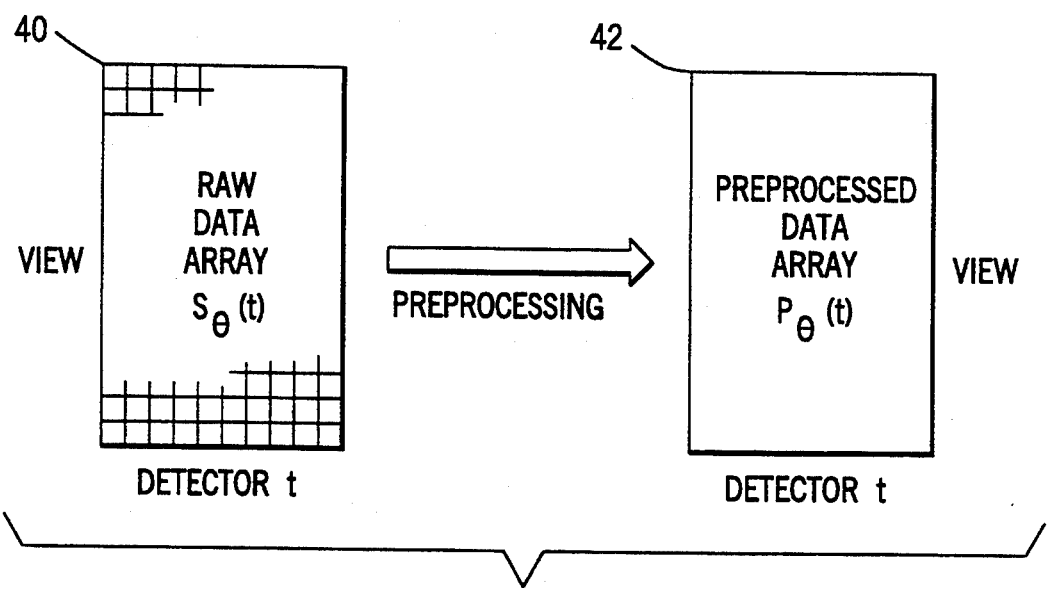
FIG. 3 depicts two arrays of X-ray attenuation data stored in the system of FIG. 1.

During the acquisition of X-ray attenuation data, the computer 26 activates the X-ray source 13 and commands the gantry motor controller 23 to cause the gantry to rotate about the patient 15. Individual views of the patient are acquired by storing the data from all of the detectors 18 at several angles as the gantry makes a 360° revolution about the patient. As shown in FIG. 3, the digitized signals from each of the detectors during a scan is stored as raw data in a storage array in the memory of the CT system. This raw data array 40 comprises a set of storage locations arranged in a two-dimensional matrix. Each row of storage locations in the array contains data from a separate view taken at a different rotational position of the gantry, and each column in array 40 contains the digital signal samples from a different detector 18. Thus, each item of data $S_\theta(t)$ in the raw data array 40 is specified by the view in which the item of data was acquired which is represented by the angle $\theta$ of the gantry for that view, and by the particular detector element (t) which acquired that item of data.

The raw data array 40 is so named because it contains the digitized signals from the detectors without dark current or beam hardening correction. The data acquisition system (DAS) 24 preprocesses the raw data in array 40 to correct beam hardening and compensate for dark current and other offset variations among the DAS signal channels. The DAS 24 performs the preprocessing necessary to generate a projection which represents the line integral of the attenuation coefficient of the patient (e.g. −log). The result of this preprocessing is an array of data $P_\theta(t)$ stored in another section of the CT system memory which is referred to as a preprocessed data array 42. Ideally, the contents of array 42 have been fully compensated for differences among the detector elements 18 and the signal channels in the DAS 24 that are associated with each detector element 18. Each data item $P_\theta(t)$ within array 42 represents a line integral of the attenuation of the X-ray beam traveling between the source 13 and the corresponding detector 18.

As noted previously, periodically the DAS 24 is calibrated to eliminate variations among the detector elements. This calibration is accomplished by activating the X-ray source 13 without any object being present between the source and the array of detectors 18 (air calibration). Any signal variation among the detectors indicates an error with respect to a given detector or its signal channels in DAS 24. Such variation is used to produce a calibration factor which is employed by the DAS during preprocessing of the image data to eliminate the effects of the variation. Such techniques and the DAS circuitry for providing the compensation are well-known. Specifically, the DAS 24 has a memory in which calibration factors are stored for each of the detectors 18.

The present invention is directed toward a technique for monitoring subsequent changes in the detector signals which require the DAS 24 to be recalibrated. In response to the detection of such a drift, the original calibration factors are changed to bring the DAS 24 back into calibration.

Figure 6A:
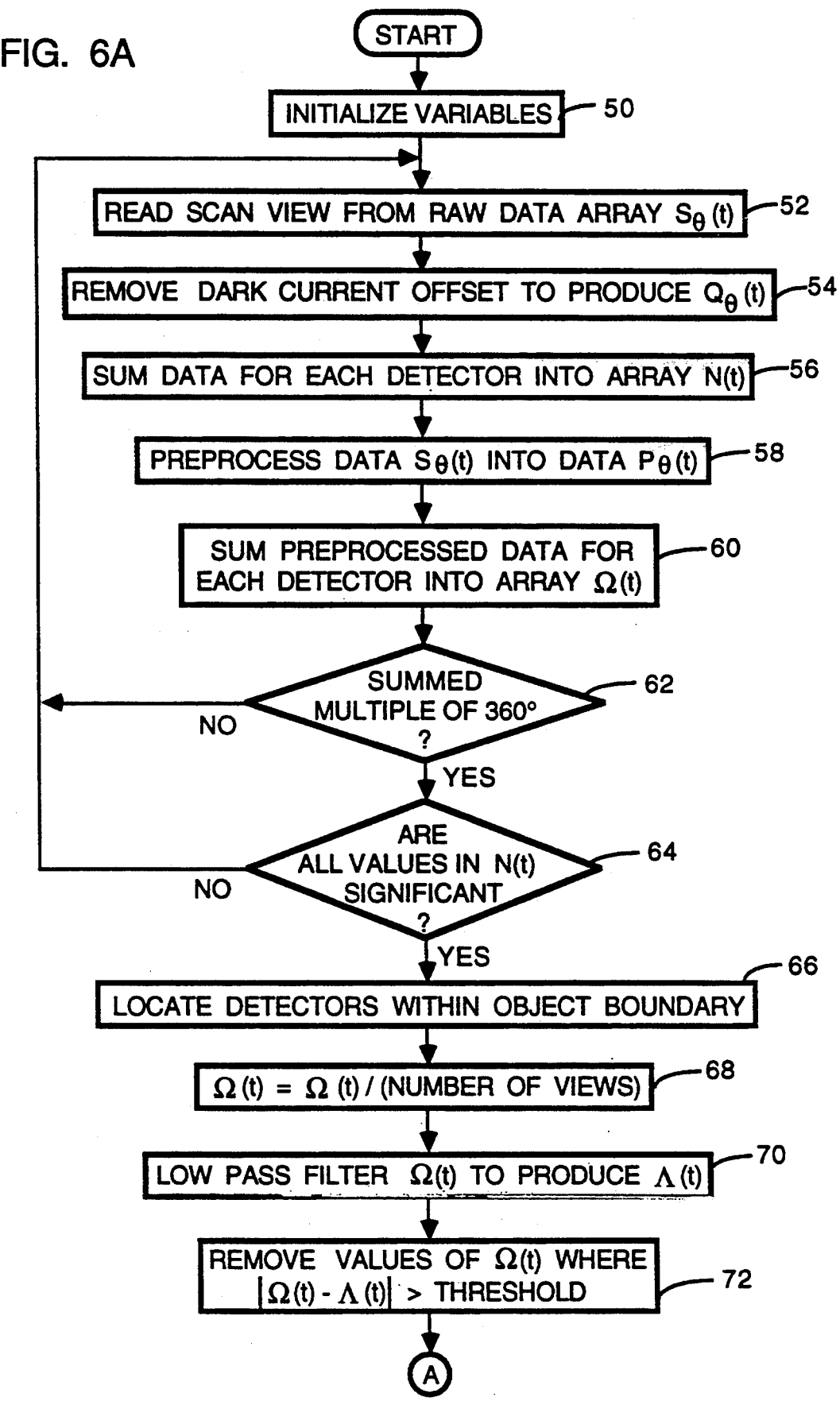
FIGS. 6A and 6B are a flowchart of the calibration software program according to the present invention.
Figure 6B:
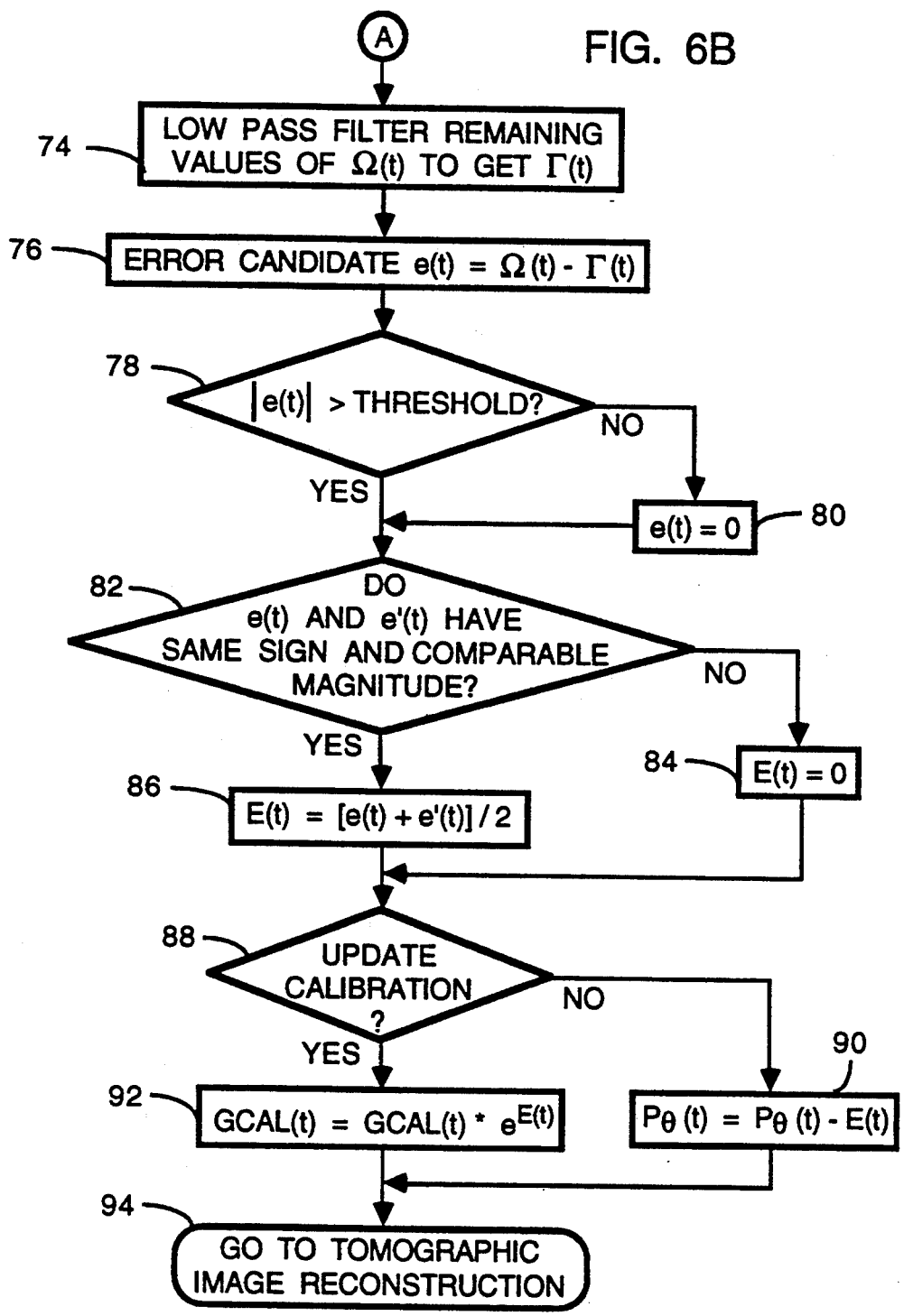

The technique used to recalibrate the DAS during acquisition of images by the CT system 10 is depicted in the flowcharts of FIGS. 6A and 6B. At the completion of one scan of the patient 15, i.e. the acquisition of X-ray attenuation data from the detectors 18 during a full 360° rotation of the gantry 12, the data has been stored in the two-dimensional raw data array 40. Thereafter, the recalibration process commences by calculating an average raw data attenuation value N(t) and an average preprocessed data value $\Omega(t)$ for each detector 18.

At step 50 all of the variables and other factors used in the recalibration process are initialized. Then the data for a given scan ($\theta$) within the raw data array 40 are read by computer 26 at step 52. The dark current offset for the associated detector 18 is removed from each data sample in the scan to produce a set of resultant data values $Q_\theta(t)$ at step 54. Next, detector by detector the resultant data value $Q_\theta(t)$ is summed with similar values for that detector from other views of the scan to produce an array N(t) containing the sums for each detector 18 at step 56.

Then at step 58, the values in raw data array 40 are processed in a conventional manner to produce the preprocessed data array 42. Once the preprocessed data array has been stored in memory, the program advances to step 60 where for each detector (t), a sum is derived of its data values $P_\theta(t)$ within the preprocessed data array 42. The summation of step 60 produces a one-dimensional array of values corresponding to the sum $\Omega(t)$ of the preprocessed data $P_\theta(t)$ for each of the detectors (t).

The program advances to step 62 where a determination is made whether data has been processed from a set of views for a multiple of an entire scan, i.e. a multiple of 360°. If not, the program execution returns to step 52 to read and process data for another view.

Once all of the data for a complete scan has been processed, the program execution advances to step 64 where each value in the array N(t) is inspected to determine whether the sum in that array for each detector exceeds a given threshold. Each such sum corresponds to the number of photons which struck the corresponding detector 18 during the scans processed by the previous steps. The number of photons striking each detector must exceed a given number in order for the acquired data to be reasonably significant for calibration purposes. For example, approximately 8,300 photons must have struck each detector. If an insufficient amount of data has been accumulated for any one of the detectors, the program execution returns to step 52 to acquire and process data from another scan. The system continues acquiring and processing scans of image data of the patient until a sufficient number of photons has struck every detector, as determined at step 64. Alternatively, the average number of photons striking the detector could be calculated at step 64 and the program advances to step 66 only when that average exceeds a given value.

Data samples from the boundary of the object being imaged have in sharp magnitude transitions and their validity may be significantly uncertain. As a consequence, it is preferable to use only data from well within the object for the present calibration technique. Therefore, data from the object boundary has to be located in the in array $\Omega(t)$ at step 66. The data within the preprocessed data array 42 can be thresholded by comparing each data item to a value that is a predefined percentage of the maximum sample value to detect the boundary transition. Alternatively, the slope at each data sample in array $\Omega(t)$ can be found and the samples with steep slopes above a given value indicate the object boundaries. Only those samples of the array $\Omega(t)$ that are within the object boundaries are used in further calibration steps. The data samples that clearly are outside the object, i.e. data samples produced by X-rays that passed only through air, can be used in conventional air-calibration of the corresponding detector signal channels. It should be noted that after scans of several patients, all of the detector signal channels in DAS 24 will have been recalibrated, either by the present recalibration technique or by conventional air-calibration methods.

Then the one-dimensional array $\Omega(t)$ representing the summation of data for each of the detector elements is processed to compute the average data value for each detector element. Specifically, at step 68, each summation value within the array $\Omega(t)$ is divided by the number of views which are utilized to create that summation. The resultant array of data also is identified as $\Omega(t)$ which array of average data is thereafter used in subsequent processing.

Figure 4:
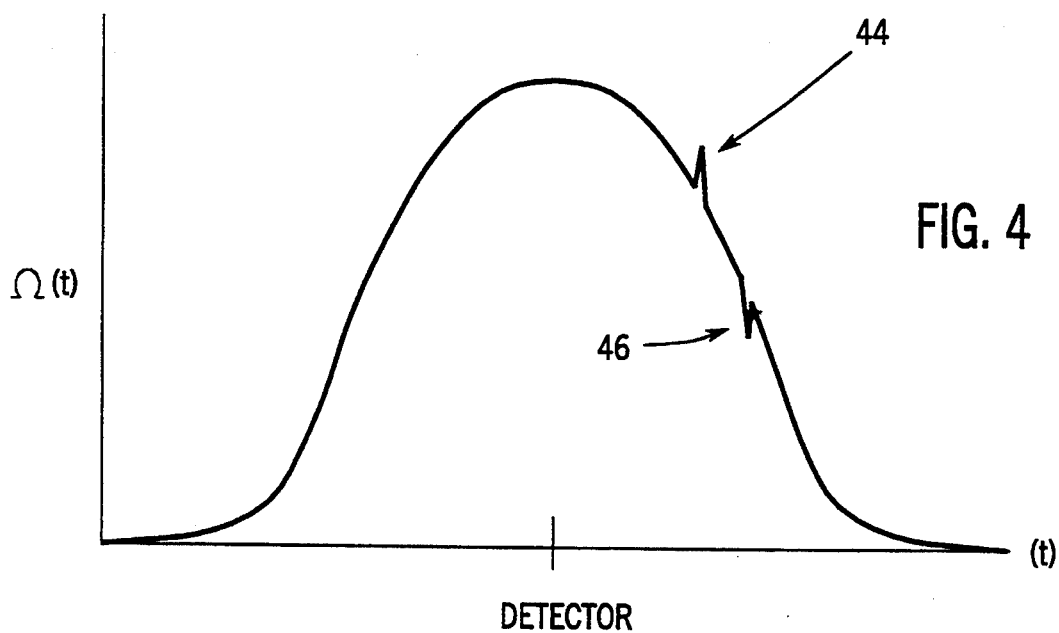
FIG. 4 is a graph of a set of data derived from the two arrays of data in FIG. 3.

Ideally, the averaged data array should have values which correspond graphically to the curve in FIG. 4. That is, the average values increase monotonically and smoothly going toward the central detector of the array and thereafter decrease monotonically going from that central detector to the other edge of the detector array 16. Any deviation from such monotonically and smoothly varying data distribution, such as shown at points 44 and 46, represents calibration errors for the corresponding radiation detectors 18. The array of data $\Omega(t)$ then is low-pass filtered at step 70 to produce an intermediate one-dimensional array $\Lambda(t)$. Any of several conventional digital low-pass filtering techniques, such as a piecewise second order polynomial fit, may be employed in the low-pass filtering step.

Once the array $\Lambda(t)$ has been determined, the computer finds data samples which appear to be very large deviations from the norm. Such large deviations often result from a major failure of a single detector or detector signal channel in the DAS and can cause a significant bias in the calibration if the resultant data is not removed from being processed. These anomalous values are found at step 72 by the computer solving the expression $|\Omega(t)-\Lambda(t)|>Z_{THRESHOLD}$. The value of $Z_{THRESHOLD}$ is determined by multiplying the local standard deviation of error by a constant. The array $\Omega(t)$ is low pass filtered again t step 74 using the same technique as before but without considering the data samples that satisfied the above expression. The low-pass filtering produces another one-dimensional array $\Gamma(t)$. Each value $\Gamma(t)$ then is subtracted the from value $\Omega(t)$ for the associated detector to detect average data values for those detectors which are out of calibration. This arithmetic operation, performed at step 76, produces a set of error values e(t).

Figure 5:
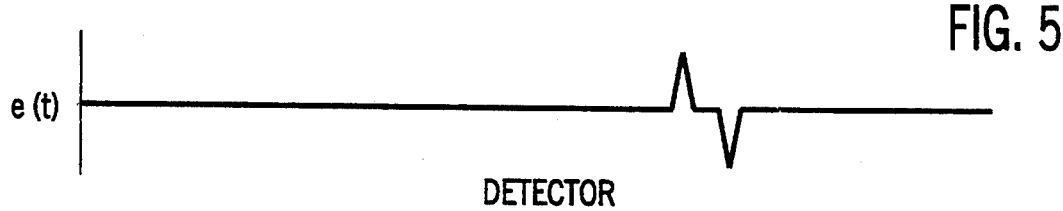
FIG. 5 represents a graph of error data derived from the data of FIG. 4.

Because the DAS circuits are constantly being calibrated during patient imaging, none of the detector signal channels should produce very large errors. Therefore, only those error values e(t) below a given magnitude indicate that recalibration of the DAS 24 for the associated detector is warranted. This thresholding guards against errors produced by other malfunctions of the system being interpreted as a detector related error. As a result, the absolute value of e(t) for each detector is compared to a threshold, at step 78. The resultant values of e(t) for the radiation detectors in array 16 are depicted on the graph of FIG. 5 with most of the values lying on or close to the zero axis. If the error value exceeds the threshold, it is set to zero at step 80. Then, a comparison is made for each detector 18 between one or more of the previous error values e'(t) and the current error value e(t), at step 82. This comparison determines whether both factors have the same sign and comparable magnitudes. For example, a comparable magnitude is indicated by the expression:

$$\frac{|e(t)| - |e'(t)|}{|e(t)| + |e'(t)|} < 0.25$$

where 0.25 is a threshold value. If these two characteristics are not satisfied, the current error value is considered a sporadic anomaly and an error factor E(t) for the associated detector is set to zero at step 84. Otherwise, the previous and current error values are averaged at step 86 which average becomes the value for the detector's error factor E(t). Thus a calibration error must persist for two consecutive executions of the calibration routine in order to produce a change in the detector's calibration factor used by DAS 24. Other techniques alternatively can be used to eliminate sporadic events from altering the calibration factors. For example, four of five consecutive error values e(t) for a given detector must have the same sign and comparable magnitude to cause recalibration to occur.

The results of the calibration process may be used either to adjust the calibration factors used in the DAS 24 to process data or to correct the preprocessed data in array 42. The user made the selection of one of these options when the CT scan was requested and the computer reads that selection at step 88. If the DAS 24 is to be recalibrated, the previous DAS calibration factor GCAL(t) for each detector is multiplied by $e^{E(t)}$ to derive a new calibration factor. The new calibration factors computed at step 92 are stored into the memory of the DAS 24. The calibration factor GCAL(t) determines the gain of an amplifier in the DAS 24 that processed the signal from the corresponding detector (t).

If the user does not want recalibration to occur, each preprocessed data value $P_\theta(t)$ is corrected by subtracting the corresponding calibration factor E(t) for the detector that produced that data value and the result is stored back into the preprocessed data array 42 at step 90. At this point, the calibration process is completed and the program execution jumps at step 94 to the tomographic image reconstruction routine.

When recalibration occurs during every scan of a patient, the calibration factors for the DAS 24 are being updated very frequently and only very small errors are introduced into the preprocessed data for any given image. Therefore, when recalibration is selected the image data need not be adjusted by subtracting the error factor from the preprocessed data.

I claim:

1. A method for calibrating signal processing circuits which process signals from an array of X-ray detectors in a computed tomography imaging system, steps of said method comprising:

acquiring an X-ray attenuation data sample from each detector in the array during each one of a plurality of views of a patient being imaged to produce a plurality of X-ray attenuation data samples for each detector;

deriving an average value for the plurality of X-ray attenuation data samples for each detector to produce a set of average values Ω(t) where t designates a given detector;

low-pass filtering the set of average values Ω(t) to produce a set of filtered values Γ(t);

for each detector t, subtracting a corresponding filtered value Γ(t) from a corresponding average value Ω(t) to produce a error value e(t); and adjusting the signal processing circuit for a given detector in response to the error value e(t) associated with that given detector.

2. The method as recited in claim 1 wherein said step of subtracting sets an error value e(t) to zero when a difference between the corresponding average value Ω(t) and the corresponding filtered value Γ(t) is greater than a predefined threshold.

3. The method as recited in claim 1 wherein said step of adjusting the signal processing circuit for a given detector comprises averaging the error value e(t) for the given detector with at least one other error value e(t) which was derived previously to produce an average error value; and altering operation of the signal processing circuit for the given detector in response to the average error value.

4. The method as recited in claim 3 wherein a gain of the signal processing circuit is defined by a calibration factor GCAL(t), and the step of altering the signal processing circuit for the given detector changes the calibration factor GCAL(t) according to the expression GCAL(t)=GCAL(t)*$e^{E(t)}$, where E(t) is a function of e(t).

5. The method as recited in claim 1 further comprising producing an image of the patient from the plurality of X-ray attenuation data samples for each detector using a tomographic reconstruction process.

6. The method as recited in claim 1 wherein said step of low-pass filtering comprises:

low-pass filtering the set of average values Ω(t) to produce an intermediate set of filtered values Λ(t);

removing a given average value Ω(t) for a given detector from the set of average values when an absolute value of a difference between the given average value Ω(t) and a value for the given detector in the intermediate set of filtered values Λ(t) is above a threshold value, thereby forming a resultant set of average values; and low-pass filtering the resultant set of average values to produce the set of filtered values Γ(t).

7. A method for calibrating a circuit which process signals from an array of X-ray detectors in a computed tomography imaging system, steps of said method comprising:

(a) acquiring a first array of X-ray attenuation data samples $S_\theta(t)$ from a plurality of views at different angles θ during a 360° scan of a patient being imaged, wherein t designates each of the detectors in the array;

(b) for each detector, summing data samples derived from the first array of X-ray attenuation data samples to produce a first set of sums N(t) in which each sum corresponds to a different detector;

(c) preprocessing the first array of X-ray attenuation data samples to produce a second array of preprocessed X-ray attenuation data samples $P_\theta(t)$, wherein the preprocessing includes multiplying each data sample by a calibration factor GCAL(t) for the corresponding detector;

(d) for each detector, summing samples in the second set of X-ray attenuation data samples to produce a second set of sums Ω(t) in which each sum corresponds to a different detector;

(e) determining from the first set of sums N(t), whether a sufficient amount of radiation has struck the array of detectors so that the second array of X-ray attenuation data samples may be used for calibration purposes;

(e) if an insufficient amount of radiation has struck the array of detectors, repeating steps (a) through (d) during which the first and second sets of sums accumulate values of the samples taken during all scans of the calibration process;

(f) when a sufficient amount of radiation has struck the array of detectors, deriving an average value of the X-ray attenuation data samples for each detector in the second set to produce a set of average values $\Omega(t)_{AVE}$;

(g) low-pass filtering the set of average values $\Omega(t)_{AVE}$ to produce a set of filtered values $\Gamma(t)$;

(h) for each detector t, subtracting a corresponding filtered value $\Gamma(t)$ from a corresponding average value $\Omega(t)_{AVE}$ to produce a error value e(t);

(i) averaging the error value e(t) with at least one other error value which was derived previously for that given detector to produce an average error value E(t); and (j) deriving a new value for each calibration factor GCAL(t) according to the expression GCAL(t)=-GCAL(t)*$e^{E(t)}$.

8. The method as recited in claim 7 wherein said step of low-pass filtering comprises:

low-pass filtering the set of average values $\Omega(t)_{AVE}$ to produce an intermediate set of filtered values $\Lambda(t)$; removing a given average value $\Omega(t)_{AVE}$ for a given detector from the set of average values when an absolute value of a difference between the given average value $\Omega(t)_{AVE}$ and a value for the given detector in the intermediate set of filtered values $\Lambda(t)$ is above a threshold value, thereby forming a resultant set of average values; and low-pass filtering the resultant set of average values to produce the set of filtered values $\Gamma(t)$.

9. The method as recited in claim 7 further comprising performing the step of deriving a new value only in response to the average error value e(t) for a given detector having a same numerical sign as a previous average error value e'(t), and in response to satisfaction of an expression:

$$\frac{|e(t)| - |e'(t)|}{|e(t)| + |e'(t)|} < T$$

where T is a threshold value.

10. The method as recited in claim 7 further comprising producing and image from the second set of X-ray attenuation data samples using a tomographic reconstruction process.

11. A method for calibrating a circuit which process signals from an array of X-ray detectors in a computed tomography imaging system, steps of said method comprising:

acquiring a set of X-ray attenuation data samples $P_\theta(t)$ from a plurality of views at different angles $\theta$ during a 360° scan of a patient being imaged, wherein t designates a particular detector in the array;

deriving an average value for the plurality of X-ray attenuation data samples for each detector to produce a set of average values $\Omega(t)$;

low-pass filtering the set of average values $\Omega(t)$ to produce a set of filtered values $\Gamma(t)$;

for each detector t, subtracting a corresponding filtered value $\Gamma(t)$ from a corresponding average value $\Omega(t)$ to produce a series of error values e(t); and correcting the attenuation data samples $P_\theta(t)$ in response to the error values e(t).

12. The method as recited in claim 11 wherein said step of subtracting sets an error value e(t) to zero when a difference between the corresponding average value $\Omega(t)$ and the corresponding filtered value $\Gamma(t)$ is greater than a predefined threshold.

13. The method as recited in claim 11 wherein said step of correcting the attenuation data samples $P_\theta(t)$ comprises averaging each error value e(t) with at least one other error value e(t), which was derived previously, to produce set of average error values; and subtracting an average error value from each of the attenuation data samples $P_\theta(t)$.

14. The method as recited in claim 11 wherein said step of low-pass filtering comprises:

low-pass filtering the set of average values $\Omega(t)$ to produce an intermediate set of filtered values $\Lambda(t)$;

removing a given average value $\Omega(t)$ for a given detector from the set of average values when an absolute value of a difference between the given average value $\Omega(t)$ and a value for the given detector in the intermediate set of filtered values $\Lambda(t)$ is above a threshold value, thereby forming a resultant set of average values; and low-pass filtering the resultant set of average values to produce the set of filtered values $\Gamma(t)$.

* * * * *